(12) United States Patent
Hines et al.

(10) Patent No.: US 6,986,761 B1
(45) Date of Patent: Jan. 17, 2006

(54) SANITARY NAPKIN HAVING CORE PREDISPOSED TO A CONVEX UPWARD CONFIGURATION

(75) Inventors: Letha Margie Hines, Cincinnati, OH (US); Robb Eric Olsen, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/383,550

(22) Filed: Feb. 3, 1995

Related U.S. Application Data (63) Continuation of application No. 08/122,114, filed on Sep. 16, 1993, now abandoned.

(51) Int. Cl.
A61F 13/15 (2006.01)
A61F 13/20 (2006.01)

(52) U.S. Cl. .................................. 604/385.1
(58) Field of Classification Search .............. 128/855; 604/365, 366, 378–380, 383, 385.1–387, 604/389, 390
See application file for complete search history.

(56) References Cited

U.S. PATENT DOCUMENTS

| | | | | |
|---|---|---|---|---|
| 2,747,575 A | 5/1956 | Mercer | ............ | 128/290 |
| 3,061,505 A | 10/1962 | Helasti | ............ | 162/109 |
| 3,343,543 A | 9/1967 | Glassman | ............ | 128/290 |
| 3,575,174 A | 4/1971 | Mogor | ............ | 128/290 |
| 3,908,659 A | 9/1975 | Wehrmeyer et al. | ......... | 128/287 |
| 4,059,114 A | 11/1977 | Richards | ............ | 128/287 |
| 4,210,144 A | 7/1980 | Sarge, III et al. | ............ | 128/287 |
| 4,285,343 A * | 8/1981 | McNair | ............ | 604/387 |
| 4,560,372 A | 12/1985 | Pieniak | ............ | 604/369 |
| 4,578,070 A | 3/1986 | Holtman | ............ | 604/378 |
| 4,596,567 A | 6/1986 | Iskra | ............ | 604/368 |
| 4,605,404 A * | 8/1986 | Sneider | ............ | 604/385.1 |
| 4,655,759 A | 4/1987 | Romans-Hess et al. | . | 604/385 R |
| 4,758,240 A * | 7/1988 | Glassman | ............ | 604/379 |
| 4,761,322 A | 8/1988 | Raley | ............ | 428/198 |
| 4,781,710 A | 11/1988 | Megison et al. | ............ | 604/378 |
| 4,790,838 A * | 12/1988 | Pigneul et al. | ............ | 604/355.1 |
| 4,795,455 A | 1/1989 | Luceri et al. | ............ | 604/386 |
| 4,840,692 A | 6/1989 | Kamstrup-Larsen | ........ | 156/252 |
| 5,009,651 A | 4/1991 | Kamishioiri et al. | ........ | 604/378 |
| 5,171,302 A | 12/1992 | Buell | ............ | 604/385.1 |
| 5,197,959 A * | 3/1993 | Buell | ............ | 604/385.1 |
| 5,211,641 A | 5/1993 | Roos et al. | ............ | 604/385.1 |
| 5,312,386 A | 5/1994 | Correa et al. | ............ | 604/379 |
| 5,366,492 A | 11/1994 | Ueki | ............ | 607/114 |

FOREIGN PATENT DOCUMENTS

| | | | |
|---|---|---|---|
| AT | 3236084 | * | 3/1985 |
| EP | 0 136 524 A1 | | 4/1985 |
| EP | 0 613 671 A2 | | 9/1994 |
| WO | 9312747 | * | 7/1993 |

* cited by examiner

Primary Examiner—Michele M. Kidwell
(74) Attorney, Agent, or Firm—Kevin C. Johnson; Larry L. Huston (57) ABSTRACT

A sanitary napkin which deforms to a convex upwardly shaped cross section. The sanitary napkin has a line of weakness which is symmetric about the longitudinal axis and longitudinally concave towards the lateral centerline. In a preferred embodiment, the line of weakness is discontinuous and comprises discrete sites joining the topsheet and core. The discrete sites may be bilaterally staggered about the line of weakness.

13 Claims, 4 Drawing Sheets

SANITARY NAPKIN HAVING CORE PREDISPOSED TO A CONVEX UPWARD CONFIGURATION

This is a continuation of application Ser. No. 08/122,114, filed on Sep. 16, 1993 abandoned.

FIELD OF THE INVENTION

This invention relates to sanitary napkins, more particularly to sanitary napkins which improve body contact through a convex upward facing configuration, and more particularly to such sanitary napkins having a core with lines of weakness therein.

BACKGROUND OF THE INVENTION

Sanitary napkins are well known in the art. Sanitary napkins intercept menses upon discharge, and thereby protect the clothing and bedding of the wearer from soiling due to the menses. However, oftentimes the sanitary napkin can shift in use and the menses will not hit the target area. Additionally, improved menses interception can occur if the sanitary napkin is in close contact with the body of the wearer.

Several attempts have been made in the art to improve body contact with the wearer, and hence absorb menses upon discharge and thereby minimize soiling by providing a sanitary napkin having a convex upward configuration. Examples of such attempts are illustrated in U.S. Pat. No. 2,747,575 issued May 29, 1956 to Mercer; U.S. Pat. No. 3,343,543 issued Sep. 26, 1967 to Glassman; U.S. Pat. No. 5,171,302 issued Dec. 15, 1992 to Buell; and U.S. Pat. No. 5,197,959 issued Mar. 30, 1993 to Buell. The two patents issued to Buell are incorporated herein by reference. However, Glassman suffers from drawbacks which are significant in sanitary napkins successfully commercialized today, and further improvements are possible over Buell.

For example, Mercer requires the sanitary napkin to have stitching through its thickness to achieve a longitudinal medial hump. Stitching a sanitary napkin according to today's construction is simply infeasible due to the materials now utilized. Also this process is prohibitively slow and costly.

Glassman requires the sanitary napkin to have longitudinal troughs on the top surface of the sanitary napkin formed by mechanical compression or cutting slits. This sanitary napkin further has a compression formed continuous groove which may or may not include the moisture resistant covering on the back of the sanitary napkin. The groove allows the sanitary napkin to fold into an inverted U-shape. The longitudinal groove, however, does not promote concave cupping of the front of the sanitary napkin around the mons pubis of the wearer and does not fit into the gluteal groove. More importantly, the continuous longitudinal groove prevents the sanitary napkin from having resiliency. Resiliency is the ability of the sanitary napkin to return to an uncompressed configuration when external deformation forces, such as the lateral pressure of the wearer's thighs, are removed. It is important that the sanitary napkin have resiliency, in order that the target area remain as large as possible, and menses does not strike the clothing of the wearer. Furthermore, the compressed groove will have a lower rate of absorbency or a lesser capacity.

Buell teaches a sanitary napkin having a deformation element with flexure hinges. The deformation element is a moldable substance such as foam and may be reformable or resilient. The deformation element and hence the sanitary napkin deforms into a W-shaped cross-section in response to lateral pressure from the wearer's thighs. The deformation element, similar to the Mercer stitching, requires an additional component to be added to the sanitary napkin, thus increasing its cost.

Furthermore, none of these attempts are suitable with particular sanitary napkins which today are commercially successful. Today's sanitary napkins frequently incorporate superabsorbents, have a caliper less than 5 millimeters, and frequently a caliper less than 3 millimeters. Such a sanitary napkin cannot readily be stitched, as taught by Mercer, due to the materials are too thin and lack strength sufficient to support the stitching. Stitching in the Z-direction is infeasible, as well as prohibitively slow and costly. Similarly, sanitary napkins will neither form a cup shape around the mons pubis of the wearer, nor be resilient if grooved on the underside because they are too flexible along the entire longitudinal length. Finally, a deformation element cannot be added to such a sanitary napkin as the caliper would significantly increase. Increased caliper increases the wearer's awareness of the sanitary napkin and decreases her comfort.

Accordingly, it is an object of this invention to provide a sanitary napkin which provides a convex upwardly facing cross-section. It is further an object of this invention to provide a sanitary napkin which is concave towards the mons pubis of the wearer. It is finally an object of this invention to provide a sanitary napkin which has resiliency without adding a separate element.

SUMMARY OF THE INVENTION

The invention comprises a sanitary napkin having mutually orthogonal longitudinal and lateral centerlines. The sanitary napkin has a liquid pervious topsheet, a liquid impervious backsheet, and an absorbent core intermediate the topsheet and the backsheet. The absorbent core has a first major face oriented towards the topsheet. In the first major face of the absorbent core is a line of weakness. The line of weakness is longitudinally concave towards the lateral centerline.

In a preferred embodiment, the first line of weakness is formed by a series of discrete sites. The discrete sites may join the topsheet and core by heat, compression, or a combination thereof.

The sanitary napkin may also have a second line of weakness concave towards said first line of weakness and concave towards the lateral centerline. The sanitary napkin may have yet additional lines of weakness concave away from the longitudinal centerline.

The first and second lines of weakness allow the sanitary napkin to deform to a convex upward configuration at the vaginal orifice and gluteal groove, and a concave upward configuration around the mons pubis of the wearer. The additional lines of weakness allow the sanitary napkin to deform to a W-shaped cross section in response to lateral pressure from the thighs of the wearer.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. It should be understood, however, that the present invention is also applicable to other feminine hygiene or catamenial pads such as panty liners, or other absorbent articles such as incontinence pads, and the like.

Figure 1:
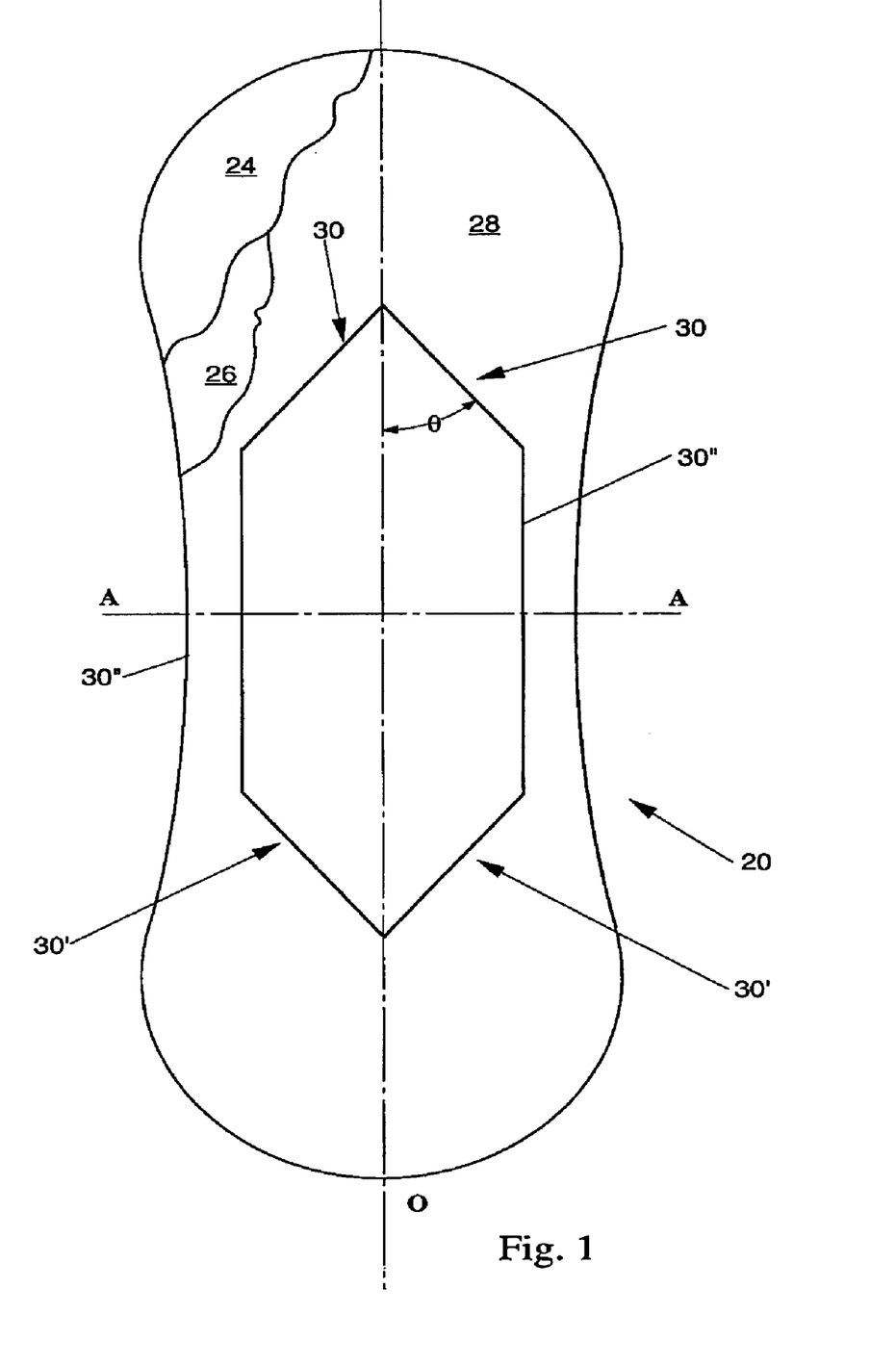
FIG. 1 is a top plan view of a sanitary napkin according to the present invention shown partially in cutaway and having a continuous line of weakness.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined with the topsheet 24, and absorbent core 28 positioned between the topsheet 24 and the backsheet 26. The absorbent core 28 has two major faces, a first major face oriented towards the topsheet 24 and a second major face oriented towards the backsheet 26. The first major face is on the tension side of the absorbent core 28 when it is deformed to a convex upwards configuration. Several lines of weakness are disposed in the core 28 on the first major face.

The sanitary napkin 20 has two centerlines, a longitudinal centerline O—O and a lateral centerline A—A. The term "longitudinal" as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 and is generally perpendicular to the longitudinal direction. The Z-direction is orthogonal both the longitudinal and lateral centerlines of the sanitary napkin 20 and extends outwardly from the plane of the sanitary napkin 20, which is defined by the longitudinal centerline O—O and lateral centerline A—A.

The long edges of the sanitary napkin 20, which are aligned with the longitudinal axis, are the longitudinal side margins of the sanitary napkin 20. The ends of the sanitary napkin 20 joining the longitudinal side margins are the transverse ends of the sanitary napkin 20. Collectively the longitudinal side margins and transverse ends of the sanitary napkin 20 define its periphery.

While the topsheet 24, the backsheet 26, and the absorbent core 28 may be assembled in a variety of well known configurations (including so called "tube" products or side flap products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924 "Bordered Disposable Absorbent Article" issued to Ahr on Mar. 30, 1982; U.S. Pat. No. 4,589,876, "Shaped Sanitary Napkin With Flaps" issued to Van Tilburg Aug. 18, 1987. Each of these patents are hereby incorporated herein by reference. The topsheet 24 and the backsheet 26 may have length and width dimensions generally larger than those of the absorbent core 28. The topsheet 24 and the backsheet 26 may extend beyond the edges of the absorbent core 28 to thereby form not only portions of the periphery but also side flaps.

The absorbent core 28 may be any absorbent means capable of absorbing or retaining liquids (e.g., menses and/or urine). The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester or polyolefin fibers; peat moss; tissue including tissue wraps and tissue laminates; absorbent foams; absorbent sponges; superabsorbent polymers; absorbent gelling materials; or any equivalent material or combinations of materials, or mixtures of these. A particularly preferred absorbent core 28 is made of thermally bonded airlaid material having approximately 15 percent synthetic fibers. Synthetic fibers are preferred due to the ease with which they fuse together to join the core 28 and topsheet 24 as described below. A particularly preferred synthetic fiber is a bi-component material having a polyethylene sheath and a polypropylene center.

The configuration and construction of the absorbent core 28 may also be varied (e.g., the absorbent core 28 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 28 should, however, be compatible with the design loading and the intended use of the sanitary napkin 20. Further, the size and absorbent capacity of the absorbent core 28 may be varied to accommodate different uses such as incontinence pads, panty liners, regular sanitary napkins, or overnight sanitary napkins.

The backsheet 26 is impervious to liquids and is preferably manufactured from a thin plastic film, although other flexible liquid impervious materials may also be used. As used herein, the term "flexible" refers to materials which are compliant and will readily conform to the general shape and contours of the human body. The backsheet 26 prevents exudates absorbed and contained in the absorbent core 28 from wetting the clothing and bedding of the wearer. The backsheet 26 may alternatively comprise a film-coated nonwoven material. Preferably, the backsheet 26 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation 161-0001, and by Tredegar Corporation, of Terre Haute, Ind., under the designation XP-39385.

The backsheet 26 has an inwardly oriented surface oriented towards the absorbent core 28 and an outwardly oriented surface opposed thereto. The outwardly oriented surface of the backsheet 26 faces, and in use contacts, the undergarment of the wearer. If desired, strips of adhesive may be joined to the outwardly facing surface of the backsheet 26 to facilitate attachment of the sanitary napkin 20 to the undergarment of the wearer.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from apertured formed films, foams, or woven and nonwoven materials comprised of natural or synthetic fibers. A preferred topsheet 24 comprises an apertured formed film as described in U.S. Pat. No. 3,929,135, entitled "Absorptive Structures Having Tapered Capillaries," which issued to Thompson on Dec. 30, 1975; U.S. Pat. No. 4,324,246 entitled "Disposable Absorbent Article Having A Stain Resistant Topsheet," which issued to Mullane, et al. on Apr. 13, 1982; U.S. Pat. No. 4,342,314 entitled "Resilient Plastic Web Exhibiting Fiber-Like Properties," which issued to Radel et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression," which issued to Ahr et al. on Jul. 31, 1984; and U.S. Pat. No. 5,006,394 entitled "Multilayer Polymeric Film," which issued to Baird on Apr. 9, 1991. Each of these patents is incorporated herein by reference.

The preferred topsheet 24 for the present invention is the formed film described in one or more of the above patents and marketed by The Procter & Gamble Company of Cincinnati, Ohio as "DRI-WEAVE" for sanitary napkins 20. For the invention described and claimed herein, it is preferred that the topsheet 24 be synthetic, so that the topsheet 24 can be joined to synthetic fibers of the absorbent core 28 by heat. For the embodiments described herein, the topsheet 24 and the core 28 may be joined at continuous or discontinuous lines of weakness 30, 30' using embossing plates having a surface temperature of about 149 to 177 degrees C. The embossing plates may be used to apply pressure to the topsheet 24 and core 28, each having synthetic materials, for about 10 seconds.

The backsheet 26 and the topsheet 24 are positioned adjacent the first and second major faces of the core 28 respectively, so that the core 28 is intermediate the backsheet 26 and topsheet 24. The backsheet 26 and topsheet 24 are preferably joined thereto and to each other by attachment means (not shown) such as are well known in the art. Adhesives which have been found to be satisfactory attachment means are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment," which issued to Minetola et al. on Mar. 4, 1986, and which is incorporated herein by reference. Alternative attachment means comprise heat, pressure, ultrasonic, and dynamic mechanical bonds.

In an alternative embodiment of the present invention, the sanitary napkin 20 has two flaps (not shown), each of which extend laterally beyond the longitudinal side margins of the sanitary napkin 20. The flaps are configured to drape over the edges of the wearer's undergarment. The flaps help prevent soiling by menstrual fluid, preferably by forming a double walled barrier along the edges of the undergarment. The flaps are preferably provided with attachment means on the garment surface, so that they can be folded back underneath the crotch of the undergarment. In this way the flaps serve to keep the sanitary napkin 20 properly positioned.

The flaps may be constructed of various materials including materials used for the topsheet 24, backsheet 26, combinations thereof, and may be a laminate having tissue in the center. Further, the flaps may be a separate element attached to the main body of the sanitary napkin 20 or can comprise extensions of the topsheet 24 and/or backsheet 26. Preferred flaps may be made in accordance with U.S. Pat. No. 4,589,876 issued May 20, 1986 to Van Tilburg or 4,687,478 issued Aug. 18, 1987 to Van Tilburg. Both of these patents are incorporated herein by reference.

The flaps extend outwardly from a proximal end joined to the sanitary napkin 20 at a distal edge. For the embodiments described herein, it is preferable that the proximal ends of the flaps be joined to the garment facing surface of the backsheet 26 of the sanitary napkin 20 at a location inboard of said longitudinal sides of said sanitary napkin 20.

The first major face of the sanitary napkin 20 has a first line of weakness 30 therein. The line of weakness 30 may be continuous or discrete. The line of weakness 30 may be made in any number of ways, such as by compression or by cutting into the core 28 of the sanitary napkin 20. The sanitary napkin 20 deforms or bends about the line of weakness 30.

The first line of weakness 30 is preferably longitudinally concave. By "longitudinally concave" it is meant that the line of weakness is symmetric about the longitudinal axis and concave in the longitudinal direction. More particularly, the line of weakness 30 is longitudinally concave towards the lateral centerline A—A of the sanitary napkin 20.

The first line of weakness 30 allows the sanitary napkin 20 to conform to a convex upward configuration, particularly the portion of the sanitary napkin 20 intercepted by the concavity of the line of weakness. This arrangement allows the sanitary napkin 20 to deform to a convex upward configuration at the vaginal orifice, in response to lateral pressure imposed by the thighs of the wearer.

The first line of weakness 30 which is longitudinally concave towards the lateral centerline A—A should be oriented to the front of the sanitary napkin 20 as it is worn. This wearing arrangement allows the sanitary napkin 20 to form a concave upward configuration around the mons pubis of the wearer.

The first line of weakness 30 forms an included angle $\Theta$ with the longitudinal axis O—O of about 15 to about 50 degrees, preferably about 20 degrees. For the embodiments described herein having a sanitary napkin 20, having an overall longitudinal length of about 21 centimeters, the first line of weakness 30 may have a length of about 2.5 to about 6.0 centimeters, as measured from the vertex on the longitudinal centerline O—O to the point of the first line of weakness 30 which is most remote from the longitudinal centerline O—O.

Figure 2:
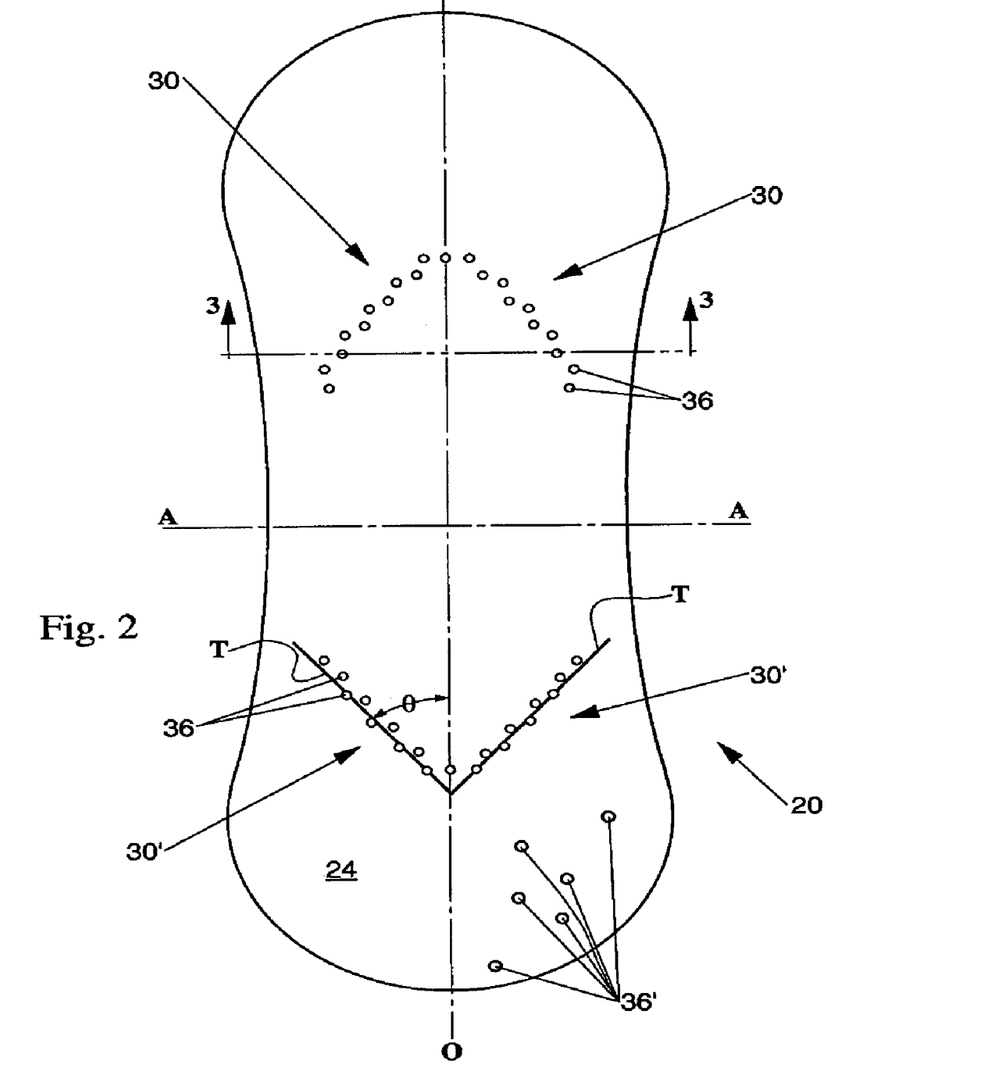
FIG. 2 is a top plan view of a sanitary napkin according to the present invention having two discontinuous lines of weakness.

In a more preferred embodiment, the sanitary napkin 20 further comprises a second line of weakness 30'. The second line of weakness 30' is also longitudinally concave towards the lateral centerline A—A. This arrangement allows the sanitary napkin 20 to be worn in either orientation without the wearer having to consider whether or not she is putting it on properly or backwards.

If desired, the first and second lines of weakness 30, 30' may be connected by longitudinally oriented, preferably longitudinally parallel, intermediate lines of weakness 30". The intermediate lines of weakness 30" may be parallel (as shown) or may be convergent/divergent if the first and second lines of weakness 30, 30' do not extend equally from the longitudinal centerline O—O.

Referring to FIG. 2, the second line of weakness 30' which is longitudinally concave towards the lateral centerline A—A is disposed in the rear of the sanitary napkin 20 as it is worn. This arrangement allows the sanitary napkin 20 to be worn in either orientation without the wearer having to consider whether or not she is putting it on properly or backwards. This arrangement provides two lines of weakness 30, 30', which may be symmetrically opposite about the lateral centerline A—A and are preferably symmetrically opposite about the longitudinal centerline O—O. Of course, as discussed below, the symmetry of the first and second lines of weakness 30, 30' does not preclude the sanitary napkin 20 according to the present invention from comprising additional lines of weakness 34 as illustrated in FIG. 4.

The first and second lines of weakness 30, 30' in FIG. 2 are defined by a series of discontinuous sites. The regions intermediate the discrete sites 36 are not weakened by compressing or cutting as described herein.

Figure 3:
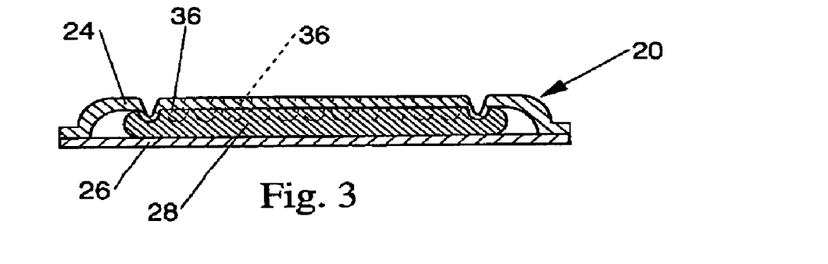
FIG. 3 is a vertical sectional view taken along line 3—3 of FIG. 2.
Figure 4:
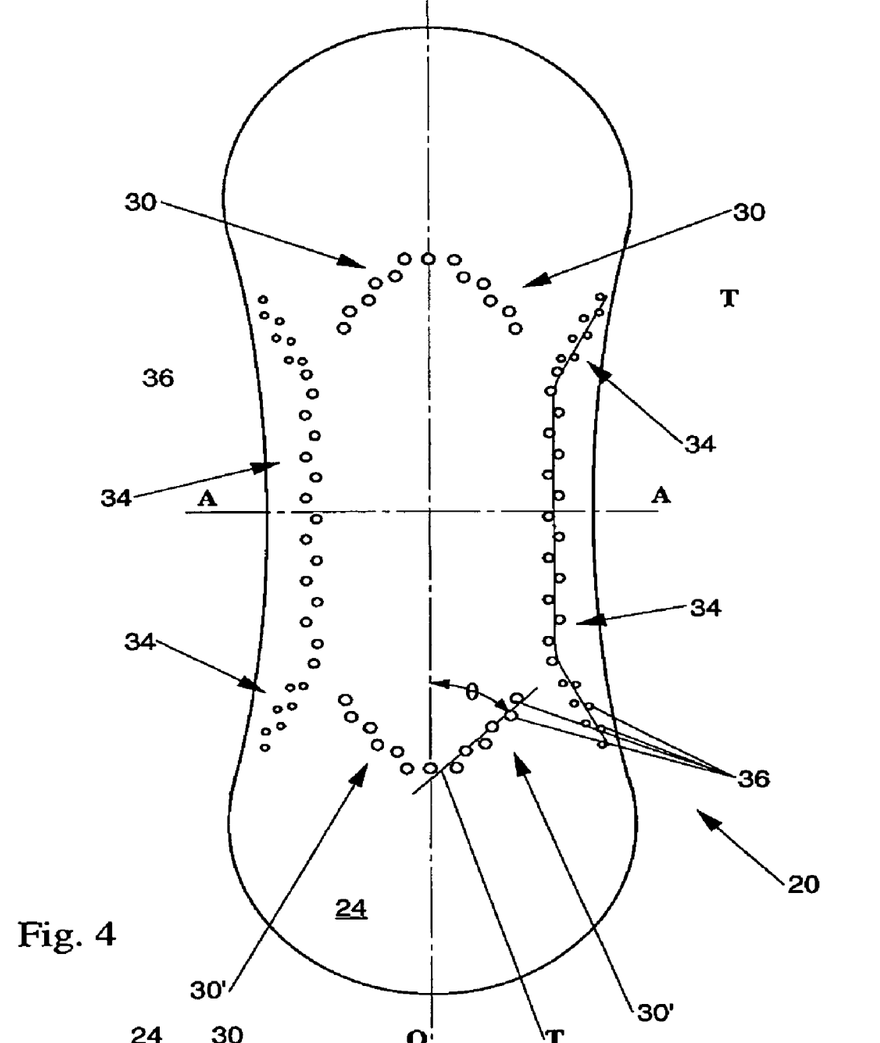
FIG. 4 is a top plan view of an alternative embodiment of the present invention having additional lines of weakness oriented convex outwardly from the longitudinal centerline.

A discontinuous line of weakness 30, 30', or 34 as shown in FIGS. 2–4 provides advantages over a continuous line of weakness 30, 30', 34. For example, either a continuous or a discontinuous line of weakness 30, 30', 34 will cause the sanitary napkin 20 to preferentially deform to the convex upward configuration described above. However, the inflection point at the discontinuous line of weakness 30, 30', 34 typically occurs at a vertex. A sharp vertex at the inflection point is generally not desirable because it destroys, or at least minimizes, the resiliency of the sanitary napkin 20 and further is less comfortable to the wearer and excessively compresses the core 28, resulting in a lesser absorbency rate or capacity.

Further, the uncompressed areas between the discrete sites 36 maintain their absorbency. The discrete sites 36 which comprise the first and second lines of weakness 30, 30' of FIGS. 2–4 may comprise any geometric shape, such as ellipses, triangles, or rectangles. However, circles are a preferred shape for the discrete sites 36 due to the consumers' aesthetic preference for feminine, round shapes. Furthermore, the absence of sharp corners on the discrete sites 36 minimizes the tendency of the topsheet 24 to tear or otherwise have undesirable stress concentrations in the topsheet 24 and core 28. If circles are selected for the shape of the discrete sites 36, the circles may range in diameter from about 1.5 to about 2.0 millimeters for the embodiments described herein, and may be spaced approximately 5 millimeters apart center to center. The discrete sites 36 may, for the embodiments described herein, be approximately 1 millimeter deep, extending through the topsheet 24 into the absorbent core 28. This arrangement provides the advantage that the adhesive commonly used to join the topsheet 24 and the core 28 may be eliminated, so that the sanitary napkin 20 is free of such adhesive.

Alternatively, additional discrete sites 36' may be dispersed throughout a portion of or the entirety of the first major face of the core 28, without conforming to or being juxtaposed with a particular line of weakness 30, 30', 34. In this embodiment, the lines of weakness 30, 30', and 34 may be formed by a higher density of discrete sites 36. The discrete sites 36 preferably comprise not more than about five percent of the surface area of the core 28.

Alternatively, as illustrated in FIG. 2, it is more preferred that the discrete sites 36 which comprise the lines of weakness 30, 30', 34 and any other discrete sites 36 present in the sanitary napkin 20 be limited to the central trisection of the sanitary napkin 20. For a sanitary napkin 20 having a core 28 with a longitudinal length of about 16 to about 21 centimeters, the discrete sites 36 which comprise the line of weakness and any other discrete sites 36 which weaken the core 28 should be limited to the region about 35 to about 55 millimeters on either side of the lateral centerline A—A.

The discrete sites 36 may be bilaterally staggered about the theoretical line of weakness T as shown. By bilaterally staggered it is meant that the theoretical line of weakness T (having no thickness) passes between the centers of the discrete sites 36 which define the line of weakness 30, 30'. Of course, segments of the discrete sites 36 may overlap the theoretical line of weakness T but the centers of the discrete sites 36 do not. This arrangement provides the advantage that a more gradual axis of bending occurs, improving the resiliency of the sanitary napkin 20 and its ability to return to provide the full target area for the wearer.

Referring to FIG. 3, in a particularly preferred embodiment, the discrete sites 36 are caused by compression of the core 28 coincident with heat. This arrangement joins the core 28 to the topsheet 24 at the discrete sites 36. Joining the core 28 and topsheet 24 together at discrete sites 36 integrates these two components of the sanitary napkin 20 into a single layer, providing for improved fluid handling properties. By having discrete sites 36 which maintain a desired core 28 structure in the uncompressed areas, menses absorbed into the core 28 of the sanitary napkin 20 can spread throughout its entirety, and not be restricted to the area of the sanitary napkin 20 intercepted by the lines of weakness 30, 30', 34, as would be the case if a continuous line were compressed into the sanitary napkin 20. However, either continuous or discontinuous lines of weakness 30, 30', 34 which join and integrate the topsheet 24 and core 28 provide for more rapid absorption of menses deposited on the topsheet 24.

Referring to FIG. 4, the sanitary napkin 20 may comprise third and fourth lines of weakness 34 disposed on opposite sides of the longitudinal centerline O—O and oriented laterally concave away from said longitudinal centerline O—O. The third and fourth lines of weakness 34 are symmetrically opposite about the longitudinal centerline O—O. The area of the core 28 intercepted by the third and fourth lines of weakness 34 deforms upwards at the longitudinal side margins in response to the lateral pressure from the wearer's thighs.

Figure 5:
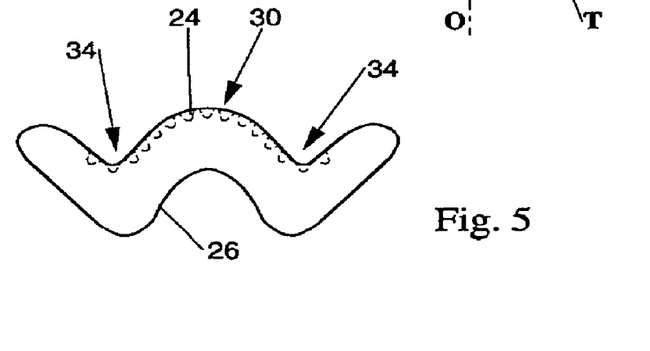
FIG. 5 is an end view of the sanitary napkin of FIG. 4 deformed to a convex upwards configuration with a W-shaped cross section.

Referring to FIG. 5, this arrangement forms a vertex at the third and fourth lines of weakness 34 so that the sanitary napkin 20 assumes and deforms to a W-shaped cross-section in response to the lateral pressure from the thighs of the wearer. This arrangement provides the advantage that better conformity to the gluteal groove of the wearer occurs. This arrangement provides the further advantage that lines of weakness 30, 30', 34 in a relatively thin sanitary napkin 20 having the arrangement shown will provide a concave upward configuration at the mons pubis, a W-shaped cross section at the vaginal opening, providing improved introital contact, and a convex upward shape at the gluteal groove. This arrangement provides the further advantage that menses wicking or flowing in the lateral direction is inhibited from flowing off the edge of the sanitary napkin 20 and soiling the clothing or bedding of the wearer. Additionally, the bending of the sanitary napkin 20 about the lines of weakness 30, 30', 34 increase the stiffness of the sanitary napkin 20, thereby reducing occurrences of foldover which diminish the target area. This arrangement is particularly advantageous on relatively long sanitary napkins 20.

Figure 6:
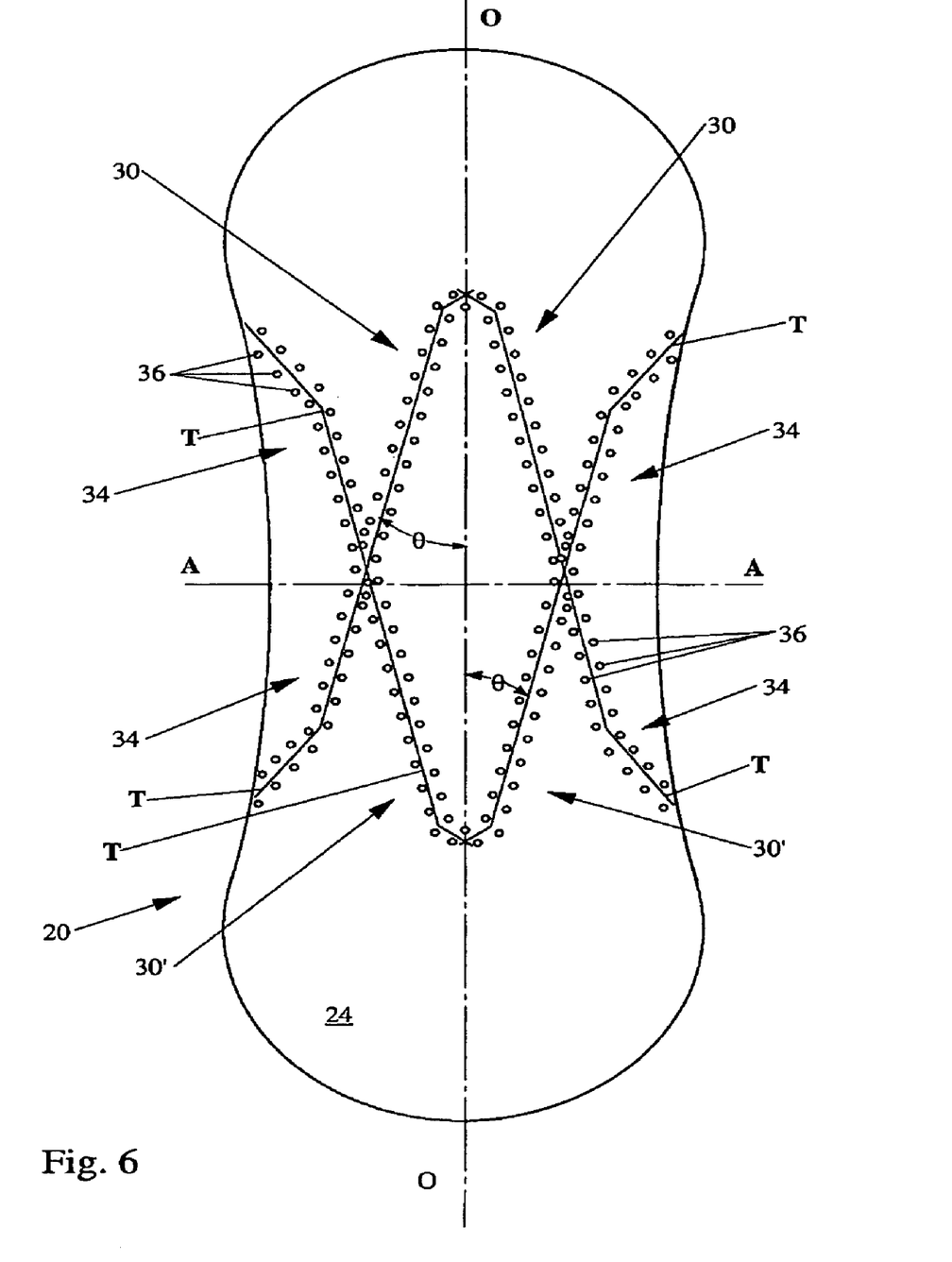
FIG. 6 is a top plan view on an alternative embodiment, similar to FIG. 4, and having both the first and second lines of weakness intercept the lateral centerline and showing the fastening adhesive in phantom. For clarity, the fastening adhesive has only been shown at one end of the sanitary napkin. However, it is to be understood the other end of the sanitary napkin may have a similar arrangement of fastening adhesive.

In use, the sanitary napkin 20 can be held in place by means well known in the art. Preferably the sanitary napkin 20 is placed in the wearer's undergarment and secured thereto by fastening adhesive 48. The fastening adhesive 48 is joined to the garment facing surface of the backsheet 26. Suitable adhesives are Century A-305-IV manufactured by Century Adhesives Corporation of Columbus, Ohio; Instant Lock 34-2823 manufactured by the National Starch and Chemical Company of Bridgewater, N.J. and XG-0176-111 manufactured by 3 Sigma of Covington, Ohio. The fastening adhesive 48 may be covered with any commercially available release liner commonly used for such purposes.

To maintain the W-shaped cross section, a preferred panty fastening adhesive 48 has a V-shape, symmetric about the longitudinal centerline O—O, and which radiates outwardly therefrom as either end of the sanitary napkin 20 is approached. A particularly preferred arrangement for such fastening adhesive 48 is disclosed in commonly assigned U.S. patent application Ser. No. 07/915,134 filed Jul. 23, 1992, in the names of Hines et al., and the corresponding international application PCT/US92/06054.

The sanitary napkin 20 may further comprise additional lines of weakness (not shown) having a V-shape and adapted to be disposed in the rear of the sanitary napkin 20 as it is worn. Such additional lines of weakness may also be symmetric about the longitudinal centerline O—O, and radiate outwardly therefrom as the end of the sanitary napkin 20 is approached.

Referring to FIG. 6, if desired, the first and second lines of weakness 30, 30' may intercept the lateral centerline A—A. In this arrangement, the first and second lines of weakness 30, 30' are connected to each other, without requiring intermediate lines of weakness 30". Such an embodiment may also have third and fourth lines of weakness 34, which intercept the first and second lines of weakness 30, 30' at the lateral centerline A—A. Such an arrangement provides two vertices coincident the lateral centerline A—A and symmetrically opposite the longitudinal centerline O—O.

While it will be apparent that many other configurations, combinations and permutations of the foregoing are feasible, and such variations fall with the scope of the appended claims.

What is claimed is:

1. A sanitary napkin having a longitudinal center line and a lateral centerline orthogonal thereto, and having longitudinal side margins and transverse ends, said sanitary napkin comprising:
    a liquid pervious topsheet;
    a liquid impervious backsheet; and
    an absorbent core intermediate said topsheet and said backsheet, said core having two major faces, a first major face oriented toward said topsheet and a second major face oriented toward said backsheet, said first major face having a discontinuous first line of weakness therein, said line of weakness being longitudinally concave towards said lateral centerline, said line of weakness comprising discrete sites, said discrete sites being bilaterally staggered about said line of weakness wherein said sanitary napkin deforms to a convex upward configuration while in use.

2. A sanitary napkin according to claim 1 wherein said line of weakness comprises compressed regions in said core.

3. A sanitary napkin according to claim 1 wherein said line of weakness comprises cuts or slits in said core.

4. A sanitary napkin according to claim 1 wherein said line of weakness joins said core and said topsheet.

5. A sanitary napkin according to claim 4 wherein said sanitary napkin is free of adhesive joining said core and said topsheet.

6. A sanitary napkin according to claim 1 further comprising second and third discontinuous lines of weakness in said core on the opposite sides of said longitudinal centerline and being laterally concave away from said longitudinal centerline, wherein said second and third lines of weakness comprise discrete sites.

7. A sanitary napkin according to claim 6 further comprising V-shaped discontinuous lines of weakness comprise discrete sites radiating outwardly from said longitudinal centerline as a said transverse end of the sanitary napkin is approached.

8. A sanitary napkin according to claim 7 further comprising flaps for attachment to an undergarment of a wearer, wherein said flaps are joined to said backsheet inboard of said longitudinal side margins of said sanitary napkin.

9. A sanitary napkin according to claim 8 further comprising two discontinuous lines of weakness symmetrically opposite about said longitudinal centerline and oriented concave outward therefrom, said two lines of weakness having a vertex juxtaposed with said lateral centerline, wherein said two lines of weakness comprise discrete sites.

10. A sanitary napkin according to claim 9 whereby said sanitary napkin deforms to a W-shaped cross section in response to lateral pressure from the thighs of the wearer.

11. A sanitary napkin having a longitudinal centerline and a lateral centerline orthogonal thereto, and having longitudinal side margins and transverse ends, said sanitary napkin comprising:
    a liquid pervious topsheet;
    a liquid impervious backsheet; and
    an absorbent core intermediate said topsheet and said backsheet, wherein said absorbent core and said topsheet are joined together at discrete sites forming a first line of weakness symmetric about said longitudinal axis and longitudinally concave towards said lateral centerline, wherein said discrete sites are bilaterally staggered about said line of weakness.

12. A sanitary napkin according to claim 11 further comprising a second discontinuous line of weakness concave towards said first line of weakness and concave towards said lateral centerline, wherein said second line of weakness is formed by discrete sites.

13. A sanitary napkin according to claim 12 further comprising discrete sites joining said core and said topsheet, said discrete sites being dispersed throughout a portion of said sanitary napkin without conforming to a line of weakness and having a lesser density than said discrete sites comprising said line of weakness.

* * * * *